United States Patent [19]

Nyfeler et al.

[11] Patent Number: 4,894,380

[45] Date of Patent: Jan. 16, 1990

[54] 2-MERCAPTO-5-PYRIDYL-1,3,4-OXADIAZOLES AND 2-MERCAPTO-5-PYRIDYL-1,3,4-THIADIAZOLES OF THE FORMULA I

[75] Inventors: Robert Nyfeler, Basel, Switzerland; Wolfgang Eckhardt, Lörrach, Fed. Rep. of Germany; Ernst Beriger, Allschwil; Odd Kristiansen, Möhlin, both of Switzerland

[73] Assignee: Ciba-Geigy Corporation, Ardsley, N.Y.

[21] Appl. No.: 176,483

[22] Filed: Mar. 25, 1988

[30] Foreign Application Priority Data

Apr. 3, 1987 [CH] Switzerland ............... 1293/87

[51] Int. Cl.$^4$ .................... C07D 413/04; A61K 31/41
[52] U.S. Cl. .................................. 514/340; 514/342; 546/277
[58] Field of Search ................. 546/277; 514/340, 342

[56] References Cited

U.S. PATENT DOCUMENTS

| | | |
|---|---|---|
| 2,744,908 | 5/1956 | Young et al. ............ 546/277 |
| 4,518,601 | 5/1985 | Kristiansen et al. ......... 546/277 |

FOREIGN PATENT DOCUMENTS

| | | |
|---|---|---|
| 0097126 | 12/1983 | European Pat. Off. ........... 546/277 |
| 2304321 | 8/1974 | Fed. Rep. of Germany. |
| 4534818 | 11/1970 | Japan .................................. 546/277 |
| 4534819 | 11/1970 | Japan .................................. 546/277 |
| 2140807 | 12/1984 | United Kingdom. |

OTHER PUBLICATIONS

Omar et al., CA 105: 226453Y.
Salama et al., CA 99: 56674Y.

*Primary Examiner*—Jane T. Fan
*Attorney, Agent, or Firm*—Edward McC. Roberts

[57] ABSTRACT

The invention relates to 2-mercapto-5-pyridyl-1,3,4-oxadiazoles and 2-mercapto-5-pyridyl-1,3,4-thiadiazoles of the formula I

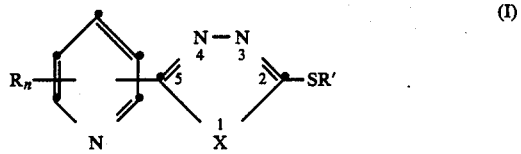

wherein
X is oxygen or sulfur,
R' is $C_1$–$C_3$alkyl which is substituted by bromine, fluorine, $C_1$–$C_3$alkoxy or cyano; unsubstituted or halogen-substituted $C_3$–$C_7$alkenyl; unsubstituted or halogen-substituted $C_4$–$C_7$alkynyl,
R is $C_1$–$C_3$alkyl, unsubstituted $C_1$–$C_3$alkoxy or $C_1$–$C_3$alkoxy which is substituted by halogen or $C_1$–$C_3$alkoxy; unsubstituted or halogen-substituted $C_3$–$C_7$alkenyl; $C_3$–$C_7$alkynyl, $C_1$–$C_3$alkylthio, halogen, cyano, hydroxy, amino or amino which is substituted by one or two $C_1$–$C_3$alkyl groups; or is aminocarbonyl; and
n is 0, 1, 2, 3 or 4, to the preparation of the compounds of formula I and to novel intermediates for the synthesis of these compounds. The compounds of formula I have nematicidal properties. The invention further relates to nematicidal compositions which contain at least one compound of formula I as active component, and to methods of using said compounds and of the compositions containing them for controlling nematodes.

24 Claims, No Drawings

2-MERCAPTO-5-PYRIDYL-1,3,4-OXADIAZOLES AND 2-MERCAPTO-5-PYRIDYL-1,3,4-THIADIAZOLES OF THE FORMULA I

The present invention relates to novel substituted 2-mercapto-5-pyridyl-1,3,4-oxadiazoles and 2-mercapto-5-pyridyl-1,3,4-thiadiazoles, to their preparation and to nematicidal compositions which contain at least one of these compounds as active ingredient. The invention further relates to novel intermediates for the synthesis of the compounds of the invention and to the use of 2-mercapto-5-pyridyl-1,3,4-oxadiazoles and 2-mercapto-5-pyridyl-1,3,4-thiadiazoles and compositions containing them for controlling nematicides, especially plant-destructive nematicides.

The 2-mercapto-5-pyridyl-1,3,4-oxadiazoles and 2-mercapto-5-pyridyl-1,3,4-thiadiazoles of this invention, and salts thereof, have the general formula I.

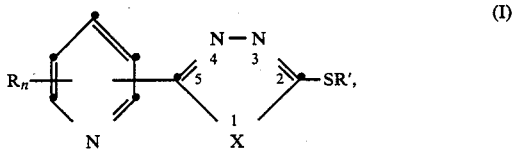

wherein
X is oxygen or sulfur,
R' is $C_1$–$C_3$alkyl which is substituted by bromine, fluorine, $C_1$–$C_3$alkoxy or cyano; unsubstituted or halogen-substituted $C_3$–$C_7$alkenyl; unsubstituted or halogen-substituted $C_4$–$C_7$alkynyl,
R is $C_1$–$C_3$alkyl; or halo-$C_1$–$C_3$alkyl; unsubstituted $C_1$–$C_3$alkoxy or $C_1$–$C_3$alkoxy which is substituted by halogen or $C_1$–$C_3$alkoxy; unsubstituted or halogen substituted $C_3$–$C_7$alkenyl; $C_3$–$C_7$alkynyl, $C_1$–$C_3$alkylthio, halogen, cyano, hydroxy, amino or amino which is substituted by one or two $C_1$–$C_3$alkyl groups; or is aminocarbonyl; and
n is 0; 1; 2; 3 or 4.

Alkyl by itself or as moiety of another substituent such as alkoxy will be understood as meaning straight chain and branched alkyl groups. Such groups include methyl, ethyl as well as the propyl and isopropyl group. Halogen-substituted alkyl is a mono- to perhalogenated alkyl group, e.g. $CHCl_2$, $CH_2F$, $CCl_3$, $CH_2Cl$; $CHFCH_3$, $CH_2CH_2Br$, $CF_2CF_3$, $C_2Cl_5$, $CH_2Br$, $CHBrCl$ and the like, and is preferably $CHF_2$. Alkenyl is typically 1-propenyl, allyl, 1-butenyl, 2-butenyl or 3-butenyl, as well as chains containing several double bonds. Alkynyl is typically 2-propynyl, 1-butynyl, 2-butynyl, 4-pentynyl and the like. Halogen is fluorine, chlorine, bromine or iodine, and is preferably fluorine, chlorine or bromine.

Examples of salt-forming inorganic acids are hydrohalic acids such as hydrofluoric acid, hydrochloric acid, hydrobromic acid or hydriodic acid, as well as sulfuric acid, phosphoric acid, phosphorous acid and nitric acid; examples of salt-forming organic acids are acetic acid, trifluoroacetic acid, trichloroacetic acid, propionic acid, glycolic acid, thiocyanic acid, lactic acid, succinic acid, citric acid, benzoic acid, cinnamic acid, oxalic acid, formic acid, benzenesulfonic acid, p-toluenesulfonic acid, methanesulfonic acid, salicylic acid, p-aminosalicylic acid, 2-phenoxybenzoic acid and 2-acetoxybenzoic acid.

Oxadiazole and thiadiazole derivatives disclosed as having nematicidal properties are known. Thus U.S. Pat. No. 3,770,754 discloses such compounds with hetero atoms in 1,2,4-position, whereas U.S. Pat. No. 4,454,147 describes 1,3,4-thiadiazole derivatives in which, as compared with the compounds of this invention, the heterocycle is substituted by a chlorine atom instead of by mercapto groups. As nematicides these known compounds have so far been unable to meet fully the demands made of them in practice. Further, oxadiazole derivatives having fungicidal properties are disclosed in German Offenlegungsschrift 2 361 613. However, this reference does not expressly mention any of these compounds that fall within the scope of formula I of the present invention.

With the compounds of formula I of the present invention it is now possible to make a valuable contribution to controlling plant nematodes which cause considerable agricultural damage to plants. By controlling such nematodes, harvest losses of cultivated plants such as potatoes, cereals, carrots, rape, cabbage and vegetables and also damage caused in nurseries and to ornamentals can be inhibited in the long term. The compounds of the present invention are distinguished in particular by the feature that they effectively control soil nematodes which parasitise on roots, e.g. those nematodes of the genera Heterodera and Globodera (cystogenic nematodes), Meloidogyne (root-knot nematodes) and also of the genera Radopholus, Pratylenchus, Longidorus, Trichodorus, and Xiphinema. The nematode genera Ditylenchus (stem parasites), Aphelenchoides (bud and leaf nematodes) and Anguina (seed-gall nematodes) can also be effectively controlled with the compounds of this invention.

Preferably the compounds of formula I are used for effectively controlling particularly harmful nematode species of the genus Meloidogyne, e.g. *Meloidogyne incognita*, of the genus Heterodera, e.g. *Heterodera glycines* (soybean cyst nematode), of the genus Globodera, e.g. *Globodera rostochienis* (potato cyst nematode), as well as representatives of migrating endoparasites such as Pratylenchus penetrans or Radopholus similis, and representatives of ectoparasites such as Trichodorus spp. and Xiphinema spp.

To control plant nematodes and for the preservation of plant health, the novel compounds may be used curatively, preventively or systemically. They have a wide activity spectrum against the various nematode species and therefore meet the requirements made of them in practice. The nematicidal mode of action of the compounds of the present invention is advantageously coupled with their low phytotoxicity, whereby the generally desirable lessening of risk to the environment is especially taken into account.

Within the scope of this invention, the following groups of compounds and individual compounds of formula I are preferred:

1. Those 2-mercapto-5-(pyid-2-yl)-1,3,4-oxadiazoles of formula Ia

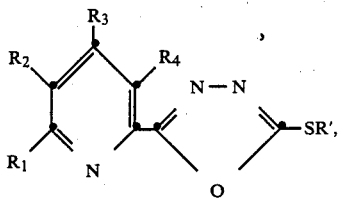

wherein R' is difluoromethyl, $R_1$, $R_2$ and $R_3$ are hydrogen and $R_4$ is aminocarbonyl or hydroxy; and also those wherein R' is difluoromethyl, cyanomethyl or propargyl, and $R_1$, $R_2$, $R_3$ and $R_4$ are hydrogen.

1.1 Among these compounds, 2-difluoromethylthio-5-(pyrid-2-yl)-1,3,4-oxadizaole is particularly preferred.

2. Those 2-mercapto-5-(pyid-2-yl)-1,3,4-thiadiazoles of formula Ib

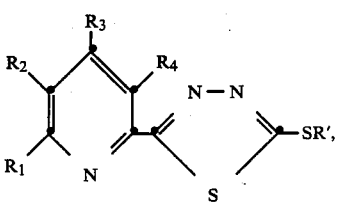

wherein R' is $C_1$–$C_3$alkyl which is substituted by bromine, fluorine or cyano; allyl or halogen-substituted allyl; $R_1$, $R_2$, $R_3$ and $R_4$ are each independently hydrogen, methyl, difluoromethyl, trifluoromethyl, methoxy, methylmercapto, chloro, cyano, hydroxy, amino or aminocarbonyl.

Among these compounds, those compounds are particularly preferred in which 2.1 $R_1$ and $R_4$ are each independently of the other hydrogen or chlorine, and $R_2$ and $R_3$ are hydrogen; and also those in which 2.2 R' is difluoromethyl, $R_1$, $R_2$ and $R_3$ are hydrogen and $R_4$ is methyl, trifluoromethyl, methoxy, chlorine, cyano, aminocarbonyl, hydroxy or amino; as well as those in which 2.3 R' is difluoromethyl, one of the substituents $R_1$, $R_2$ and $R_3$ is methyl, chlorine, methoxy or methylmercapto and the other two substituents are hydrogen and $R_4$ is hydrogen; and, finally those in which 2.4 R' is difluoromethyl, $R_1$ and $R_4$ are each independently of the other hydrogen, chlorine, methoxy or hydroxy, and $R_2$ and $R_3$ are hydrogen.

2.4.1. Among this last mentioned group of compounds, 2-difluoromethyltio-5-(pyrid-2-yl)-1,3,4-thiadiazole is particularly preferred.

3.1 Those 2-mercapto-5-(pyrid-2-yl)-1,3,4-oxadiazoles of formula Ic

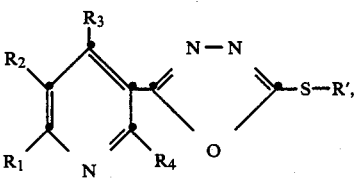

wherein R' is difluoromethyl and one of the substituents $R_1$, $R_2$, $R_3$ and $R_4$ is methyl, methylmercapto or halogen and the others are hydrogen; and those wherein 3.2 R' is difluoromethyl and two of the substituents $R_1$ to $R_4$ are each independently of the other methyl or chlorine and $R_2$ and $R_3$ are hydrogen; as well as those wherein 3.3 R' is difluoromethyl, $R_1$ and $R_4$ are chlorine and one of the substituents $R_2$ and $R_3$ is hydrogen or chlorine; and finally, 3.4 difluoromethylthio-5-(pyrid-2-yl)-1,3,4-oxadiazole.

4.1 Those 2-mercapto-5-(pyrid-3-yl)-thiadiazoles of formula Id

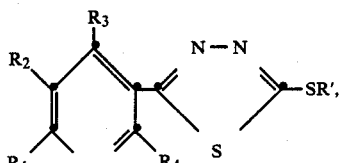

wherein R' is difluoromethyl or difluoromethyldifluoromethyl and $R_1$, $R_2$, $R_3$ and $R_4$ are hydrogen; and also those wherein 4.2 R' is difluoromethyl, $R_1$ is hydrogen, $C_1$–$C_3$alkyl or chlorine, $R_2$ is hydrogen and $R_3$ and $R_4$ are each independently of the other hydrogen or chlorine or methoxy; and finally, those wherein 4.3 R' is difluoromethyl, $R_1$, $R_2$ and $R_4$ are each independently hydrogen, chlorine, bromine, methylthio or amino, and $R_3$ is hydrogen.

4.3.1 Among this last mentioned group, 2-difluoromethylthio-5-(pyrid-3-yl)-1,3,4-thiadiazole is particularly preferred.

5. Those 2-mercapto-5-(pyrid-4-yl)-oxadiazoles of formula Ie

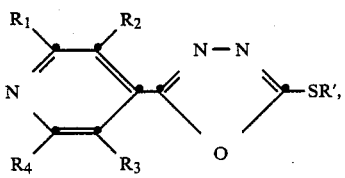

wherein R' is difluoromethyl, difluoromethyldifluoromethyl or cyanomethyl, and $R_1$, $R_2$, $R_3$ and $R_4$ are hydrogen.

6. Those 2-mercapto-5-(pyrid-4-yl)-thiadiazoles of formula If

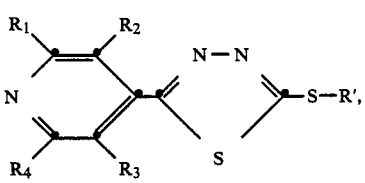

wherein $R_2$ and $R_3$ are hydrogen.

6.1 Among these compounds, those compounds are particularly preferred in which R' is difluoromethyl, difluoromethyldifluoromethyl, cyanomethyl or 2-bromoallyl, $R_1$ is hydrogen, $C_1$–$C_4$alkyl, chlorine, methoxy or methylmercapto, $R_4$ is hydrogen, methyl, chlorine, methoxyethoxy, trifluoromethylmethoxy, methylmercapto, amino or $C_1$–$C_3$monoalkylamino.

6.2 Among this last mentioned group of compounds, 2-difluoromethylthio-5-(pyrid-4-yl)-1,3,4-thiadiazole is particularly preferred.

The compounds of formula I are prepared by
(a) condensing a compound of formula II

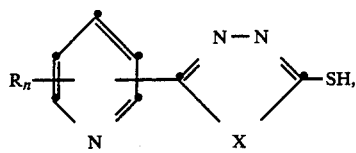

or a compound of formula III

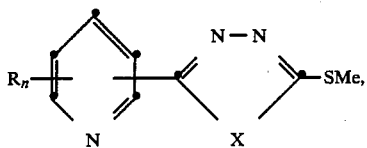

with a compound of formula IV

Hal—R'  (IV)

in an inert solvent or mixture of solvents at room temperature or at elevated temperature, in the absence or presence of a catalyst and under normal or elevated pressure, the reaction being carried out in the presence of a base if the starting material is a compound of formula II; or (b) reacting a compound of formula II

with a compound of formula V

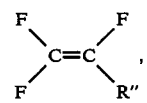

in an inert solvent or mixture of solvents at elevated temperature and in the absence or presence of a catalyst and under normal or elevated pressure, by means of an addition reaction to give a compound of formula Ig

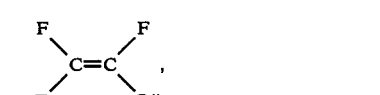

or a compound of formula Ih

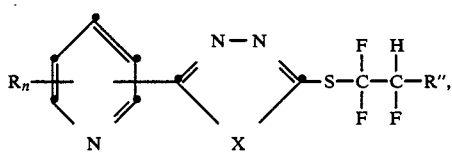

in which formulae II, III, IV, V, Ig and Ih above Me is an alkali metal or ammonium, Hal is halogen, preferably chlorine, bromine or iodine, and R" is fluorine or trifluoromethyl, and R, R' and n are defined for formula I.

Examples of solvents or diluents suitable for the preparation of the compounds of this invention are ethers and etheral compounds such as dialkyl ethers (diethyl ether, diisopropyl ether, tert-butylmethyl ether and the like), anisole, dioxane, tetrahydrofuran; aliphatic and aromatic hydrocarbons such as benzene, toluene, petroleum ether; halogenated hydrocarbons such as chlorobenzene, mehylene chloride, chloroform, ethylene chloride, carbon tetrachloirde, tetrachloroethylene; nitriles such as acetonitrile, propionitrile; N,N-dialkylated amides such as dimethylformamide; dimethyl sulfoxide; ketones such as acetone, diethyl ketone, methyl ethyl ketone; and also water and alcohols such as methanol, ethanol, isopropanol or butanol; and, quite generally, mixtures of such solvents with one another.

Suitable bases are both organic and inorganic bases; e.g. preferably tertiary amines such as trialkylamines (trimethylamine, triethylamine, tripropylamine and others), as well as oxides, hydroxides, carbonates and bicarbonates of alkali metals and alkaline earth metals (e.g. CaO, BaO, NaOH, KOH, Ca(OH)$_2$, KHCO$_3$, NaHCO$_3$, Ca(HCO$_3$)$_2$, K$_2$CO$_3$, Na$_2$CO$_3$ etc.), and also acetates such as CH$_3$COONa or CH$_3$COOK. Further suitable bases are alkali metal alcoholates such as sodium methylate, sodium propylate, potassium tert-butylate or sodium ethylate.

The addition of catalytic amounts of a crown ether, e.g. 18-crown-6 or 15-crown-5 promotes the reaction course of the preparatory processes. The catalytic addition of tetraalkylamine salts, e.g. tetraalkylamino chlorides or bromides, preferably tetra-n-butylamino bromide, is also useful for the same purpose. In addition, alkali metal iodides, preferably potassium iodide, may be used with advantage as catalysts.

The reaction temperatures in the preparatory processes are in the range from 10° to 90° C., preferably from 30° to 80° C. The reaction has to be carried out under atmospheric or under elevated pressure.

Some of the starting compounds of formula II are known and some are novel. Novel compounds are those 2-mercapto-5-pyrid-2-yl-1,3,4-oxadiazole of formula IIa'

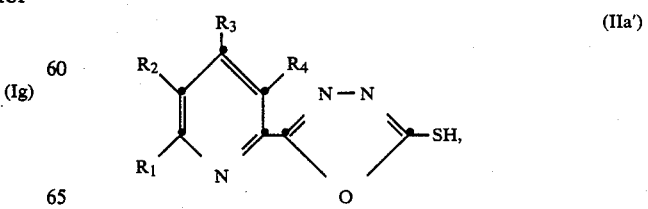

2-mercapto-5-pyrid-2-yl-1,3,4-thiadiazoles of formula IIb'

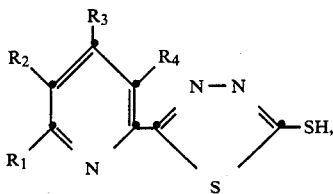

2-mercapto-5-pyrid-3-yl-1,3,4-oxadiazoles of formula IIc'

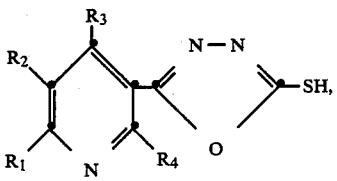

2-mercapto-5-pyrid-3-yl-1,3,4-thiadiazoles of formula IId'

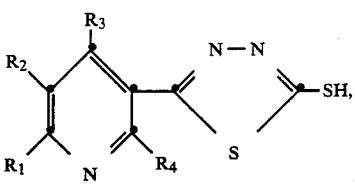

2-mercapto-5-pyrid-4-yl-1,3,4-oxadiazoles of formula IIe'

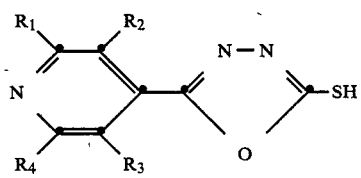

and 2-mercapto-5-pyrid-4-yl-1,3,4-thiadiazoles of formula IIf'

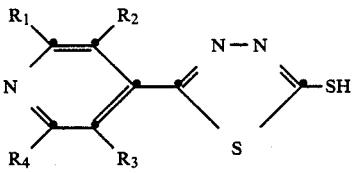

wherein $R_1$, $R_2$, $R_3$ and $R_4$ are each independently methyl, propyl or isopropyl, unsubstituted $C_1$-$C_3$alkoxy or $C_1$-$C_3$alkoxy which is substituted by halogen or $C_1$-$C_3$alkoxy, unsubstituted or halogen-substituted $C_3$-$C_7$alkenyl; or are $C_4$-$C_7$alkynyl, $C_1$-$C_3$alkylthio, halogen, cyano, hydroxy, amino or amino which is substituted by one or two $C_1$-$C_3$alkyl groups; or are aminocarbonyl.

The novel compounds of formulae IIa' to IIf' (q.v. Table 0) are intermediates for the preparation of useful nematicides and thus constitute an object of the present invention.

The starting compounds of formula II can be prepared by known methods [Salama et al: Egypt J. Chem. 1981 (Pub. 1982) 24 (1-3) 47-51 CA. 99, 53674 y (1983): Pol. J. Pharmacol. Pharm. 1981, 33(5), 527-32, CA. 97, 6229 f, 1982; Chem. Pharm. Bull. 1970, 18(8), 1696-8, CA. 73, 98877 w, 1970] or by methods analogous thereto.

The compounds of formulae IV and V are known, commercially available products.

The invention also relates to compositions for controlling plantdestructive nematodes and also for protecting plants from attack by nematodes, which compositions contain compounds of formula I.

The present invention also relates to the preparation of nematicidal compositions, which comprises homogeneously mixing compounds of formula I with one or more of the carriers and adjuvants described herein. The invention further relates to a method of treating plants, which comprises applying thereto the compounds of formula I''

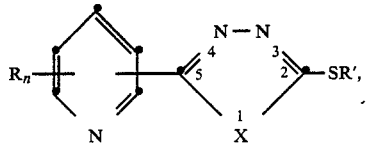

wherein
X is oxygen or sulfur,
R is hydrogen, $C_1$-$C_3$alkyl, $C_1$-$C_3$alkoxy which is substituted by halogen or $C_1$-$C_3$alkoxy; $C_3$-$C_7$alkenyl or halogen-substituted $C_3$-$C_7$alkenyl; $C_3$-$C_7$alkynyl, $C_1$-$C_3$alkylthio, cyano, hydroxy, amino or amino which is substituted by one or two $C_1$-$C_3$alkyl groups; or is aminocarbonyl,
R' is $C_1$-$C_3$alkyl which is substituted by halogen, $C_1$-$C_3$alkoxy or cyano; $C_3$-$C_7$alkenyl or halogen-substituted $C_3$-$C_7$alkenyl; unsubstituted or halogen-substituted $C_3$-$C_7$alkynyl; and
n is 0, 1, 2, 3 or 4,
or the novel compositions.

A preferred method of applying a compound of formula I or I'' or a nematicidal composition containing at least one of these compounds is soil application, which comprises treating the locus of the plants with a liquid or solid formulation.

The compounds of formula I'' may also be applied to seeds (dressing/coating) either by impregnating the seeds in a liquid formulation of the active ingredient or by coating them with a solid formulation. Moreover, in special cases, further types of application are also possible, e.g. selective treatment of the plant stems, buds or leaves.

The compounds of formula I'' are normally applied in the form of compositions and can be applied to the crop area or plant to be treated, simultaneously or in succession, with further compounds. These further compounds can also include other substances applied in agriculture which are used to increase production by promoting the growth of useful plants. Examples of such substances are fertilisers, herbicides, insecticides, fungicides, mollusicides and the like, or mixtures of several of these substances, if desired, together with further carriers, surfactants or other application promoting adjuvants customarily employed in the art of formulation.

Suitable carriers and adjuvants can be solid or liquid and correspond to the substances ordinarily employed in formulation technology, e.g. natural or regenerated mineral substances, solvents, dispersants, wetting agents, tackifiers, thickeners, binders or fertilisers.

The compounds of formula I″ are used in unmodified form or, preferably, together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the nature of the compositions, the methods of application, such as spraying, dusting, scattering or pouring, are chosen in accordance with the intended objectives and the prevailing circumstances. Advantageous rates of application are normally from 500 g to 6 kg of active ingredient (a.i.) per hectare, preferably from 1 to 4 kg a.i./ha.

The formulations, i.e. the compositions containing the compound (active ingredient) of formula I″ and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hyrdocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil, sunflower oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of formula I″ to be formulated, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloalaiphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamino-propylene glycol and alkylpolypropylene glycol containing 1 to 10 carbon atoms in the alkyl chain, which adducts contact 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethyleneethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in "McCutcheon's Detergents and Emulsifiers Annual", MC Publishing Corp., Ridgewood, N.J., 1979; Dr. Helmut Stache, "Tensid Taschenbuch" (Handbook of Surfactants), Carl Hanser Verlag, Munich/Vienna, 1981.

The agrochemical compositions usually contain 0.1 to 99% by weight, preferably 0.1 to 95% by weight, of a compound of formula I, 99.9 to 1% by weight, preferably 99.8 to 5% by weight, of a solid or liquid adjuvant, and 0 to 25% by weight, preferably 0.1 to 25% by weight, of a surfactant.

Whereas commercial products will preferably be formulated as concentrates, the end user will normally employ dilute formulations.

The compositions may also contain further auxiliaries such as stabilisers, antifoams, viscosity regulators, binders, tackifiers as well as fertilisers or other active ingredients for obtaining special effects.

Such agrochemical compositions constitute an object of the present invention.

The invention is illustrated in more detail by the following nonlimitative Examples.

I. Preparatory Examples

Example 0.4

2-Mercapto-5-(pyrid-3-yl)-1,3,4-oxadiazole

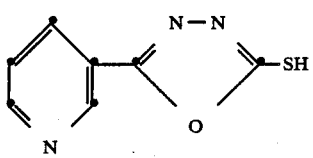

13.7 g (0.1 mol) of nicotinic acid hydrazide and 8 g (0.105 mol) of carbon disulfide are added dropwise to a solution of 56 g (0.1 mol) of potassium hydroxide in 20 g of water and 350 ml of 95% ethanol. The reaction mixture is refluxed for 3 hours, then the solvent is evaporated off under vacuum and the residue is dried under a high vacuum. The dry residue is stirred in 75 ml of water, filtered, and the filtrate is neutralised with 1N hydrochloric acid. The precipitated product is isolated by filtration, washed in succession with acetone and hexane and vacuum dried, affording 9.9 g (55% of theory) of the title compound with a melting point of 237° C.

Example 1.1

2-Difluoromethylthio-5-pyrid-2-yl-1,3,4-thiadiazole

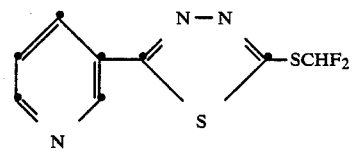

A suspension of 341.5 g (1.75 mol) of 2-mercapto-5-pyrid-2-yl-1,3,4-thiadiazole in 4000 ml of dioxane is added to a solution of 230.5 g of 85% potassium hydroxide in 800 ml of water. Then 10 g of potassium iodide and 6 g of tributylammonium bromide are added to the reaction mixture and 750 g (~8.6 mol) of gaseous difluoromethane are introduced over 4½ hours at 22°–37° C. After evaporating off the dioxane, the reaction mixture is diluted with ethyl acetate, the aqueous phase is separated and the organic solution is washed cold with 1N sodium hydroxide and water, dried over sodium sulfate and clarified with activated carbon. They ethyl acetate is removed under vacuum and the residue is crystallised from ethyl acetate/hexane, affording 321.9 g (75.1%) of the title compound with a melting point of 90°–92° C.

The following compounds of this invention can be prepared in accordance with the foregoing Preparatory Examples and with the processes described above. These compounds serve to illustrate the invention and imply no limitation thereof.

TABLE 0

| Compound | Q | X | Phys. data |
|---|---|---|---|
| 0.1 | pyrid-3-yl | —S— | m.p. >200° C. |
| 0.2 | pyrid-3-yl | —O— | m.p. >200° C. |
| 0.3 | pyrid-4-yl | —S— | m.p. 276–279° C. |
| 0.4 | pyrid-4-yl | —O— | m.p. 237° C. |
| 0.5 | pyrid-2-yl | —S— | m.p. >200° C. |
| 0.6 | pyrid-2-yl·HCl | —O— | m.p. >200° C. |
| 0.7 | 2,6-dichloropyrid-4-yl | —S— | m.p. 192–194° C. |
| 0.8 | 2,6-dichloropyrid-4-yl | —O— | m.p. 202–205° C. |
| 0.9 | 2-chloro-6-methoxypyrid-4-yl | —S— | m.p. 215–218° C. |

TABLE 0-continued $$\underset{X}{Q-\overset{N-N}{\diagdown}-SH}$$

| Compound | Q | X | Phys. data |
|---|---|---|---|
| 0.10 | 2-Cl, 6-OCH₂CH₂OCH₃ pyridin-3-yl | —S— | m.p. 153–156° C. |
| 0.11 | 2-Cl, 6-OCH₂CF₃ pyridin-3-yl | —S— | |
| 0.12 | 3-CONH₂, 2-methyl pyridin-? | —S— | |
| 0.13 | 4-Cl, 6-CH₃, 2-Cl pyridin-3-yl | —S— | |
| 0.14 | 4-OCH₃, 2-OCH₃ pyridin-3-yl | —S— | |
| 0.15 | 4-Cl, 6-Cl pyridin-3-yl | —S— | |
| 0.16 | 4-Cl, 6-CH₃ pyridin-3-yl | —S— | |
| 0.17 | 6-Cl pyridin-3-yl | —S— | |
| 0.18 | 3-Cl pyridin-2-yl | —S— | |
| 0.19 | 3-CH₃ pyridin-2-yl | —S— | |
| 0.20 | 4-OH, 6-Cl pyridin-3-yl | —S— | |
| 0.21 | 4-OCH₃, 6-Cl pyridin-3-yl | —S— | |
| 0.22 | 4-Cl, 6-Cl pyridin-3-yl | —S— | |
| 0.23 | 5-Br pyridin-3-yl | —S— | m.p. >200° C. |
| 0.24 | 6-Cl pyridin-3-yl | —S— | |
| 0.25 | 2-SCH₃ pyridin-3-yl | —S— | m.p. >200° C. |
| 0.26 | 2-Cl pyridin-3-yl | —S— | |

TABLE 0-continued $$Q-\overset{N-N}{\underset{X}{\diagdown\diagup}}-SH$$

| Compound | Q | X | Phys. data |
|---|---|---|---|
| 0.27 | 3-methyl-2-(methylthio)pyridin-yl | —O— | m.p. >200° C. |
| 0.28 | 3-bromo-5-methylpyridin-yl | —O— | m.p. >200° C. |
| 0.29 | pyridazin-yl | —O— | m.p. >200° C. |
| 0.30 | 2-methyl-pyridin-yl | —S— | m.p. >250° C. |
| 0.31 | 2-methyl-pyridin-yl | —O— | m.p. >250° C. |

TABLE 1

$$\underset{R_1}{\overset{R_2}{\underset{N}{\bigotimes}}}\overset{R_3}{\underset{X}{\overset{R_4}{-}}}\overset{N-N}{\underset{X}{\diagdown\diagup}}-SR'$$

| Compound | R' | $R_1$ | $R_2$ | $R_3$ | $R_4$ | X | Physical data |
|---|---|---|---|---|---|---|---|
| 1.1 | —$CHF_2$ | H— | H— | H— | —H | —S— | m.p. 90–92° C. |
| 1.2 | —$CHF_2$ | H— | H— | H— | —H | —O— | m.p. 82–84° C. |
| 1.3 | —$CHF_2$ | $CH_3$— | H— | H— | —H | —S— | |
| 1.4 | —$CHF_2$ | H— | $CH_3$— | H— | —H | —S— | |
| 1.5 | —$CHF_2$ | H— | H— | $CH_3$— | —H | —S— | |
| 1.6 | —$CHF_2$ | H— | H— | H— | —$CH_3$ | —S— | |
| 1.7 | —$CHF_2$ | Cl— | H— | H— | —H | —S— | |
| 1.8 | —$CHF_2$ | H— | H— | H— | —Cl | —S— | |
| 1.9 | —$CHF_2$ | H— | H— | H— | —CN | —S— | |
| 1.10 | —$CHF_2$ | H— | H— | H— | —$CONH_2$ | —S— | |
| 1.11 | —$CHF_2$ | H— | H— | H— | —$CONH_2$ | —O— | |
| 1.12 | —$CHF_2$ | H— | H— | $OCH_3$— | —H | —S— | |
| 1.13 | —$CHF_2$ | $CH_3O$— | H— | H— | —H | —S— | |
| 1.14 | —$CHF_2$ | H— | H— | H— | —$CF_3$ | —S— | |
| 1.15 | —$CHF_2$ | H— | Cl— | H— | —H | —S— | |
| 1.16 | —$CHF_2$ | H— | H— | Cl— | —H | —S— | |
| 1.17 | —$CH_2C\equiv CH$— | H— | H— | H— | —H | —S— | m.p. 87–87° C. |
| 1.18 | —$CH_2C\equiv CH$— | H— | H— | H— | —H | —O— | |
| 1.19 | —$CH_2C\equiv CH$— | H— | H— | H— | —Cl | —S— | |
| 1.20 | —$CH_2CH=CH_2$ | H— | H— | H— | —H | —S— | |
| 1.21 | —$CH_2\overset{Br}{\underset{|}{C}}=CH_2$ | H— | H— | H— | —H | —S— | m.p. 87–88° C. |
| 1.22 | —$C_3H_7(i)$ | H— | H— | H— | —H | —S— | |
| 1.23 | —$CF_2CHF_2$ | H— | H— | H— | —H | —S— | |
| 1.24 | —$CF_2CHF_2$ | Cl— | H— | H— | —H | —S— | |
| 1.25 | —$CHF_2$ | Cl— | H— | H— | —Cl | —S— | |
| 1.26 | —$CHF_2$ | Cl— | H— | H— | —Cl | —O— | |
| 1.27 | —$CHF_2$ | Cl— | H— | H— | —$OCH_3$ | —S— | |
| 1.28 | —$CHF_2$ | Cl— | H— | H— | —OH | —S— | |
| 1.29 | —$CHF_2$ | H— | H— | H— | —OH | —S— | |
| 1.30 | —$CHF_2$ | H— | H— | H— | —OH | —O— | |
| 1.31 | —$CHF_2$ | H— | H— | H— | —$OCH_3$ | —S— | |

TABLE 1-continued

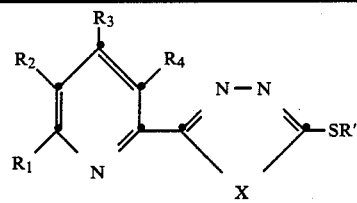

| Compound | R' | $R_1$ | $R_2$ | $R_3$ | $R_4$ | X | Physical data |
|---|---|---|---|---|---|---|---|
| 1.32 | —CHF$_2$ | H— | H— | H— | —NH$_2$ | —S— | |
| 1.33 | —CHF$_2$ | CH$_3$S— | H— | H— | —H | —S— | |
| 1.34 | —CH$_2$CN | H— | H— | H— | —H | —S— | |
| 1.35 | —CH$_2$CN | H— | H— | H— | —H | —O— | |
| 1.36 | —CBrF$_2$ | H— | H— | H— | —H | —S— | |
| 1.37 | CBrF$_2$ | H— | H— | H— | —H | —O— | |
| 1.38 | —CH$_2$CH$_2$CF=CF$_2$ | H— | H— | H— | —H | —S— | m.p. 63–66° C. |
| 1.39 | —CH$_2$CH$_2$CF=CF$_2$ | H— | H— | H— | —H | —O— | m.p. 44–45° C. |
| 1.40 | —CH$_2$CH$_2$CF=CF$_2$ | H— | H— | H— | —J | —O— | |
| 1.41 | —CH$_2$CH$_2$CF=CF$_2$ | H— | H— | H— | —J | —S— | |
| 1.42 | —CHF$_2$ | H— | H— | H— | —J | —O— | |
| 1.43 | —CHF$_2$ | H— | H— | H— | —J | —S— | |

TABLE 2

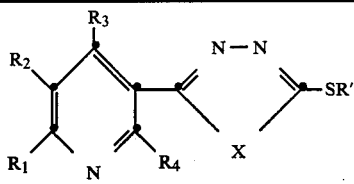

| Compound | R' | $R_1$ | $R_2$ | $R_3$ | $R_4$ | X | Physical data |
|---|---|---|---|---|---|---|---|
| 2.1 | —CHF$_2$ | H— | H— | H— | —H | —S— | m.p. 86° C. |
| 2.2 | —CHF$_2$ | H— | H— | H— | —H | —O— | $n_D^{20}$: 1.5715 |
| 2.3 | —CHF$_2$ | CH$_3$— | H— | H— | —Cl | —S— | |
| 2.4 | —CHF$_2$ | CH$_3$— | H— | H— | —Cl | —O— | |
| 2.4 | —CHF$_2$ | Cl— | H— | Cl— | —H | —S— | |
| 2.6 | —CHF$_2$ | Cl— | H— | Cl— | —H | —O— | |
| 2.7 | —CHF$_2$ | H— | H— | OCH$_3$— | —OCH$_3$ | —S— | |
| 2.8 | —CHF$_2$ | CH$_3$— | H— | Cl— | —Cl | —S— | |
| 2.9 | —CHF$_2$ | CH$_3$— | H— | Cl— | —Cl | —O— | |
| 2.10 | —CH$_2$≡CH | H— | H— | H— | —H | —S— | wax |
| 2.11 | —CF$_2$CHF$_2$ | H— | H— | H— | —H | —S— | m.p. 95–98° C. |
| 2.12 | —CHF$_2$ | Cl— | H— | H— | —Cl | —S— | |
| 2.13 | —CHF$_2$ | Cl— | H— | H— | —Cl | —O— | |
| 2.14 | —CHF$_2$ | C$_3$H$_7$(n)— | H— | H— | —Cl | —S— | |
| 2.15 | —CHF$_2$ | Cl— | Cl— | H— | —Cl | —S— | |
| 2.16 | —CHF$_2$ | Cl— | Cl— | H— | —Cl | —O— | |
| 2.17 | —CHF$_2$ | H— | Br— | H— | —NH$_2$ | —S— | |
| 2.18 | —CHF$_2$ | H— | H— | H— | —NH$_2$ | —S— | |
| 2.19 | —CHF$_2$ | H— | Br— | H— | —H | —S— | m.p. 125–127° C. |
| 2.20 | —CHF$_2$ | H— | Br— | H— | —H | —O— | m.p. 100–101° C. |
| 2.21 | —CHF$_2$ | Cl— | H— | H— | —H | —S— | |
| 2.22 | —CHF$_2$ | Cl— | H— | H— | —H | —O— | |
| 2.23 | —CHF$_2$ | H— | H— | H— | —SCH$_3$ | —S— | m.p. 69–71° C. |
| 2.24 | —CHF$_2$ | H— | H— | H— | —SCH$_3$ | —O— | m.p. 58–60° C. |
| 2.25 | —CH$_3$ | H— | H— | H— | —H | —O— | m.p. 59–64° C. |
| 2.26 | —C$_2$H$_5$ | H— | H— | H— | —H | —O— | m.p. 67–69° C. |
| 2.27 | —CH(CH$_3$)$_2$ | H— | H— | H— | —H | —O— | $n_D^{20}$: 1.5830 |
| 2.28 | —CH$_2$—CH=CH$_2$ | H— | H— | H— | —H | —O— | m.p. 62–64° C. |
| 2.29 | —CH$_2$C≡CH | H— | H— | H— | —H | —O— | m.p. 68–71° C. |
| 2.30 | —CH$_2$CN | H— | H— | H— | —H | —O— | m.p. 123–125° C. |
| 2.31 | —CH$_2$CN | H— | H— | H— | —H | —S— | |
| 2.32 | —CBrF$_2$ | H— | H— | H— | —H | —S— | |
| 2.33 | —CBrF$_2$ | H— | H— | H— | —H | —O— | |
| 2.34 | —CHF$_2$ | CH$_3$— | H— | H— | —H | —S— | |
| 2.35 | —CHF$_2$ | CH$_3$— | H— | H— | —H | —O— | |
| 2.36 | —CH$_2$CH$_2$CF=CF$_2$ | CH$_3$— | H— | H— | —H | —O— | |
| 2.37 | —CH$_2$CH$_2$CF=CF$_2$ | CH$_3$— | H— | H— | —H | —S— | |
| 2.38 | —CH$_2$CH$_2$CF=CF$_2$ | H— | H— | H— | —H | —O— | |
| 2.39 | —CH$_2$CH$_2$CF=CF$_2$ | H— | H— | H— | —H | —S— | |
| 2.40 | —CHF$_2$ | CF$_3$— | H— | H— | —H | —O— | |
| 2.41 | —CHF$_2$ | CF$_3$— | H— | H— | —H | —S— | |

TABLE 2-continued

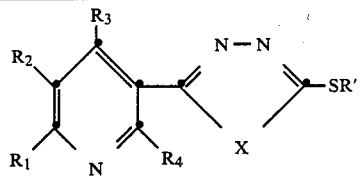

| Compound | R' | $R_1$ | $R_2$ | $R_3$ | $R_4$ | X | Physical data |
|---|---|---|---|---|---|---|---|
| 2.42 | $-CH_2CH_2CF=CF_2$ | $CF_3-$ | H— | H— | —H | —O— | |
| 2.43 | $-CH_2CH_2CF=CF_2$ | $CF_3-$ | H— | H— | —H | —S— | |

TABLE 3

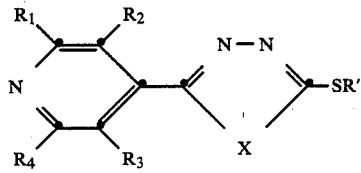

| Compound | R' | $R_1$ | $R_2$ | $R_3$ | $R_4$ | X | Physical data |
|---|---|---|---|---|---|---|---|
| 3.1 | $-CHF_2$ | H— | H— | H— | H | —S— | m.p. 87–90° C. |
| 3.2 | $-CHF_2$ | Cl— | H— | H— | —Cl | —S— | m.p. 59–62° C. |
| 3.3 | $-CHF_2$ | Cl— | H— | H— | —Cl | —O— | |
| 3.4 | $-CHF_2$ | $CH_3-$ | H— | H— | —Cl | —S— | |
| 3.5 | $-CHF_2$ | Cl— | H— | H— | —H | —S— | |
| 3.6 | $-CHF_2$ | $OCH_3-$ | H— | H— | —H | —S— | |
| 3.7 | $-CHF_2$ | $CH_3-$ | H— | H— | —H | —S— | |
| 3.8 | $-CHF_2$ | $OCH_3$ | H— | H— | —Cl | —S— | m.p. 82–85° C. |
| 3.9 | $-CHF_2$ | Cl— | H— | H— | $-OCH_2CH_2OCH_3$ | —S— | m.p. 76–79° C. |
| 3.10 | $-CH_2C\equiv CH$ | Cl— | H— | H— | —Cl | —S— | m.p. 134–137° C. |
| 3.11 | $-CH_2C\equiv CH$ | H— | H— | H— | —H | —S— | |
| 3.12 | $-CH_2C\equiv CH$ | $OCH_3-$ | H— | H— | —Cl | —S— | m.p. 131–133° C. |
| 3.13 | $-CH_2C\equiv CH$ | Cl— | H— | H— | $-OCH_2CH_2OCH_3$ | —S— | m.p. 119–121° C. |
| 3.14 | $-CH_2\overset{Br}{C}=CH_2$ | H— | H— | H— | —H | —S— | |
| 3.15 | $-CH_2\overset{Br}{C}=CH_2$ | Cl— | H— | H— | —Cl | —S— | oil |
| 3.16 | $-CH_2\overset{Br}{C}=CH_2$ | $OCH_3-$ | H— | H— | —Cl | —S— | m.p. 46–49° C. |
| 3.17 | $-CH_2\overset{Br}{C}=CH_2$ | Cl— | H— | H— | $-OCH_2CH_2OCH_3$ | —S— | oil |
| 3.18 | $-CHF_2$ | Cl— | H— | H— | $-OCH_2CF_3$ | —S— | oil |
| 3.19 | $-CF_2CHF_2$ | H— | H— | H— | —H | —S— | |
| 3.20 | $-CF_2CHF_2$ | Cl— | H— | Hi | —Cl | —S— | |
| 3.21 | $-CF_2CHF_2$ | H— | H— | H— | —H | —O— | |
| 3.22 | $-CHF_2$ | $n-C_3H_7-$ | H— | H— | —Cl | —S— | |
| 3,23 | $-CHF_2$ | Cl— | H— | H— | $-NHCH_3$ | —S— | |
| 3.24 | $-CHF_2$ | Cl— | H— | H— | —OH | —S— | |
| 3.25 | $-CHF_2$ | Cl— | H— | H— | $-NH_2$ | —S— | |
| 3.26 | $-CHF_2$ | Cl— | H— | H— | $-NHC_2H_5$ | —S— | |
| 3.27 | $-CHF_2$ | Cl— | H— | H— | $-NHC_3H_7(i)$ | —S— | |
| 3.28 | $-CHF_2$ | $CH_3-$ | H— | H— | $-CH_3$ | —S— | |
| 3.29 | $-CHF_2$ | $SCH_3-$ | H— | H— | $-SCH_3$ | —S— | |
| 3.30 | $-CH_2CN$ | H— | H— | H— | —H | —S— | |
| 3.31 | $-CH_2CN$ | H— | H— | H— | —H | —O— | |
| 3.32 | $-CBrF_2$ | H— | H— | H— | —H | —S— | |
| 3.33 | $-CBrF_2$ | H— | H— | H— | —H | —O— | |
| 3.34 | $-CH_2CH_2CF=CF_2$ | Cl— | H— | H— | —Cl | —O— | oil |
| 3.35 | $-CH_2CH_2CF=CF_2$ | H— | H— | H— | —H | —O— | $n_D^{25}$ 1.5527 |
| 3.36 | $-CHF_2$ | H— | H— | H— | —H | —O— | m.p. 88–93° C. |

2. Formulation Examples for liquid active ingredients of formula I
(throughout, percentages are by weight)

2.1. Emulsifiable concentrates

| | (a) | (b) | (c) |
|---|---|---|---|
| a compound of Tables 1–3 | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexanone | — | 15% | 20% |
| xylene mixture | 65% | 25% | 20% |

Emulsions of any required concentration can be produced from such concentrates by dilution with water.

2.2. Solutions

| | (a) | (b) | (c) | (d) |
|---|---|---|---|---|
| a compound of Tables 1–3 | 80% | 10% | 5% | 95% |
| ethylene glycol monomethyl ether | 20% | — | — | — |
| polyethylene glycol (mol. wt. 400) | — | 70% | — | — |
| N—methyl-2-pyrrolidone | — | 20% | — | — |
| epoxidised coconut oil | — | — | 1% | 5% |
| petroleum distillate (boiling range 160–190° C.) | — | — | 94% | — |

These solutions are suitable for application in the form of microdrops.

2.3. Granulates

| | (a) | (b) |
|---|---|---|
| a compound of Tables 1–3 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

2.4. Dusts

| | (a) | (b) |
|---|---|---|
| a compound of Tables 1–3 | 2% | 5% |
| highly dispersed silicic acid | 1% | 5% |
| talcum | 97% | — |
| kaolin | — | 90% |

Ready-for use dusts are obtained by intimately mixing the carriers with the active ingredient.

Formulation Examples for solid active ingredients of formula I
(throughout, percentages are by weight)

2.5. Wettable powders

| | (a) | (b) | (c) |
|---|---|---|---|
| a compound of Tables 1–3 | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

2.6. Emulsifiable concentrate

| | |
|---|---|
| a compound of Tables 1–3 | 10% |
| octylphenol polyethylene glycol ether (4–5 moles of ethylene oxide) | 3% |
| calcium dodecylbenzenesulfonate | 3% |
| castor oil polyglycol ether (35 moles of ethylene oxide) | 4% |
| cyclohexanone | 30% |
| xylene mixture | 50% |

Emulsions of any required concentration can be obtained from this concentrate by dilution with water.

2.7. Dusts

| | (a) | (b) |
|---|---|---|
| a compound of Tables 1–3 | 5% | 8% |
| talcum | 95% | — |
| kaolin | — | 92% |

Ready-for-use dusts are obtained by mixing the active ingredient with the carrier, and grinding the mixture in a suitable mill.

2.8. Extruder granulate

| | |
|---|---|
| a compound of Tables 1–3 | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

2.9. Coated granulate

| | |
|---|---|
| a compound of Tables 1–3 | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granulates are obtained in this manner.

2.10. Suspension concentrate

| | |
|---|---|
| a compound of Tables 1–3 | 40% |
| ethylene glycol | 10% |
| nonylphenol polyethylene glycol (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

Biological Example

3.1 Action against Meloidogyne incognita on tomato plants

Eggs of Meloidogyne incognita are mixed into sand. This mixture is then put into 200 ml earthenware pots (5000 eggs per pot). On the same day a three-week-old tomato plant is planted in each pot and the formulated test compound is introduced into the pots by drench application (0.0006% of active ingredient, based on the volume of the soil). The potted plants are stood in a greenhouse at a temperature of 26±1° C. and a relative humidity of 60%. After 4 weeks evaluation is made by examining the plants for root-knot formation in accordance with the Knot Index.

Compounds of Tables 1 to 3 exhibit good activity against Meloidogyne incognita in that they substantially reduce root-knot formation. On the other hand, untreated and infected control plants exhibit severe root-knot formation (=100%). Thus, in this test, e.g. compounds 1.1, and 2.11 inhibit root-knot formation almost completely (0-10% infestation).

What is claimed is:

1. A 2-mercapto-5-pyridyl-1,3,4-oxadiazole or 2-mercapto-5-pyridyl-1,3,4-thiadiazole of the formula (I)

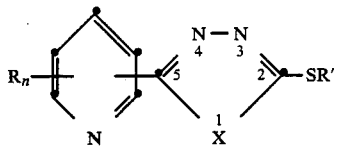

wherein

X is oxygen or sulfur,

R' is $C_1$-$C_3$alkyl which is substituted by bromine, fluorine, $C_1$-$C_3$alkoxy or cyano; unsubstituted or halogen-substituted $C_3$-$C_7$alkenyl; halogen-substituted $C_4$-$C_7$alkynyl, R is $C_1$-$C_3$alkyl; or halo-$C_1$-$C_3$alkyl unsubstituted $C_1$-$C_3$alkoxy or $C_1$-$C_3$alkoxy which is substituted by halogen or $C_1$-$C_3$alkoxy; unsubstituted or halogen-substituted $C_3$-$C_7$alkenyl; $C_3$-$C_7$alkynyl, $C_1$-$C_3$alkylthio; halogen; cyano; hydroxy, amino or amino which is substituted by one or two $C_1$-$C_3$alkyl groups; or is aminocarbonyl; and n is 0, 1, 2, 3 or 4, or a salt thereof.

2. A 2-mercapto-5-(pyrid-2-yl) 1,3,4-oxadiazole according to claim 1 of the formula

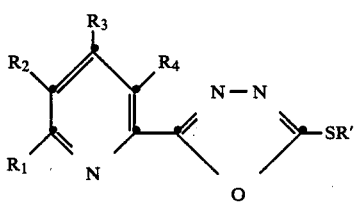

wherein R' is difluoromethyl, the substituents $R_1$, $R_2$ and $R_3$ are hydrogen and $R_4$ is aminocarbonyl or hydroxy.

3. A 2-mercapto-5-(pyrid-2-yl)-1,3,4-oxadiazole according to claim 1 of the formula

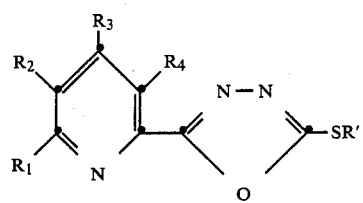

wherein R' difluoromethyl or cyanomethyl and $R_1$, $R_2$, $R_3$ and $R_4$ are hydrogen.

4. 2-Difluoromethylthio-5-(pyrid-2-yl)-1,3,4-oxadiazole according to claim 1.

5. A 2-mercapto-5-(pyrid-2-yl)thiadiazole according to claim 1 of the formula

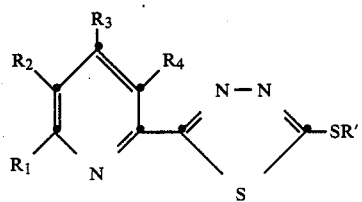

wherein R' is $C_1$-$C_3$alkyl which is substituted by bromine, fluorine or cyano; allyl or halogen-substituted allyl; $R_1$, $R_2$, $R_3$ and $R_4$ are each independently hydrogen, methyl, difluoromethyl, trifluoromethyl, methoxy, methylmercapto, chlorine, cyano, hydroxy, amino or aminocarbonyl.

6. A compound according to claim 5, wherein $R_1$ and $R_2$ are each independently of the other hydrogen or chlorine and $R_2$ and $R_3$ are hydrogen.

7. A compound according to claim 5, wherein R' is difluoromethyl, $R_1$, $R_2$ and $R_3$ are hydrogen and $R_4$ is methyl, trifluoromethyl, methoxy, chlorine, cyano, aminocarbonyl, hydroxy or amino.

8. A compound according to claim 5, wherein R' is difluoromethyl, one of the substituents $R_1$, $R_2$ and $R_3$ is methyl, chlorine, methoxy or methylmercapto and the other two substituents are hydrogen and $R_4$ is hydrogen.

9. A compound according to claim 5, wherein R' is difluoromethyl, $R_1$ and $R_4$ are each independently of the other hydrogen, chlorine, methoxy or hydroxy, and $R_2$ and $R_3$ are hydrogen.

10. 2-Difluoromethylthio-5-(pyrid-2-yl)-1,3,4-thiadiazole according to claim 9.

11. A 2-mercapto-5-(pyrid-3-yl)oxadiazole according to claim 1 of the formula

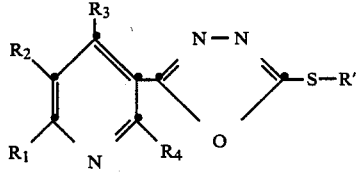

wherein R' is difluoromethyl and one of the substituents $R_1$, $R_2$, $R_3$ and $R_4$ is methyl, methylmercapto or halogen and the other three sustituents are hydrogen.

12. A 2-mercapto-5-(pyrid-3-yl)oxadiazole according to claim 1 of the formula

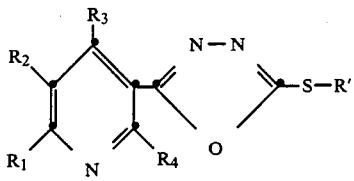

wherein R' is difluoromethyl and $R_1$ and $R_4$ are each independently of the other methyl or chlorine and $R_2$ and $R_3$ are hydrogen.

13. A 2-mercapto-5-(pyrid-3-yl)oxadiazole according to claim 1 of the formula

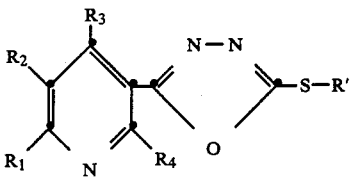

wherein R' is difluoromethyl, $R_1$ and $R_4$ are chlorine and one of the substituents $R_2$ and $R_3$ is hydrogen or chlorine.

14. A 2-mercapto-5-(pyrid-3-yl)oxadiazole according to claim 1 of the formula

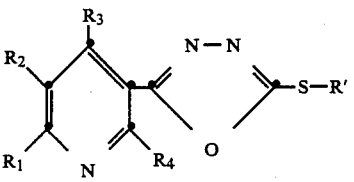

wherein R' is difluoromethyl and $R_1$, $R_2$, $R_3$ and $R_4$ are hydrogen.

15. A 2-mercapto-5-(pyrid-3-yl)thiadiazole according to claim 1 of the formula

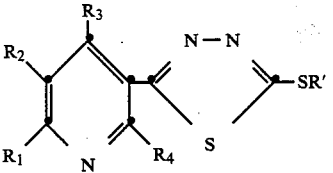

wherein R' is difluoromethyl or difluoromethyldifluoromethyl and $R_1$, $R_2$, $R_3$ and $R_4$ are hydrogen.

16. A 2-mercapto-5-(pyrid-3-yl)-thiadiazole according to claim 1 of the formula

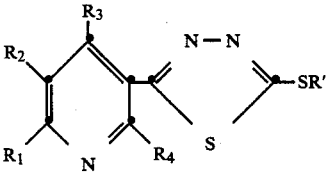

wherein R' is difluoromethyl, $R_1$ is hydrogen, $C_1$–$C_3$alkyl or chlorine, $R_2$ is hydrogen and $R_3$ and $R_4$ are each independently of the other hydrogen or chlorine or methoxy.

17. A 2-mercapto-5-(pyrid-3-yl)thiadiazole of the formula

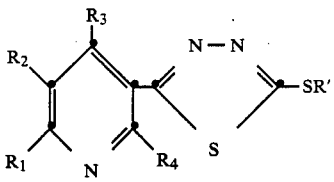

according to claim 16, wherein R' is difluoromethyl, $R_1$, $R_2$ and $R_4$ are each independently hydrogen, chlorine, bromine, methylthio or amino, and $R_3$ is hydrogen.

18. 2-Difluoromethylthio-5-(pyrid-3-yl)-1,2,4-thiadiazole according to claim 17.

19. A 2-mercapto-5(pyrid-4-yl)-oxadiazole according to claim 1 of the formula

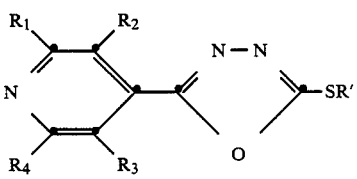

wherein R' is difluoromethyl, difluoromethyldifluoromethyl or cyanomethyl, and $R_1$, $R_2$, $R_3$ and $R_4$ are hydrogen.

20. A 2-mercapto-5-(pyrid-4-yl)-thiadiazole according to claim 1 of the formula

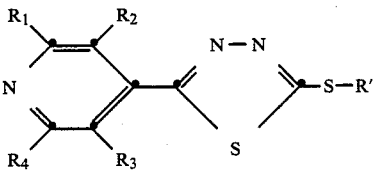

wherein $R_2$ and $R_3$ are hydrogen.

21. A compound according to claim 20, wherein R' is difluoromethyl, difluoromethyldifluoromethyl, cyanomethyl or 2-bromoallyl, $R_1$ is hydrogen, $C_1$–$C_4$alkyl, chlorine, methoxy or methylmercapto, $R_4$ is hydrogen, methyl, chlorine, methoxyethoxy, trifluoromethylmethoxy, methylmercapto, amino or $C_1$–$C_3$monoalkylamino.

22. Difluoromethylthio-5-(pyrid-4-yl)-1,3,4-thiadiazole according to claim 21.

23. A pesticidal composition for controlling nematodes or for protecting plants from attack by nematodes, which composition contains as active component a pesticidally active amount of at least one compound of claim 1.

24. A method of controlling nematodes or of protecting cultivated plants from attack by nematodes, which method comprises applying to the plant or to the locus thereof a compound of the formula

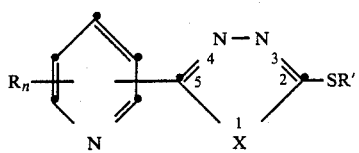

wherein

X is oxygen or sulfur

R is hydrogen, $C_1$-$C_3$alkyl, $C_1$-$C_3$alkoxy which is substituted by halogen or $C_1$-$C_3$alkoxy; $C_3$-$C_7$alkenyl or halogen-substituted $C_3$-$C_7$alkenyl; $C_3$-$C_7$alkynyl; $C_1$-$C_3$alkylthio; cyano, halogen, hydroxy; amino or amino which is substituted by one or two $C_1$-$C_3$alkyl groups; or is aminocarbonyl, R' is $C_1$-$C_3$alkyl which is substituted by halogen, $C_1$-$C_3$alkoxy or cyano; $C_3$-$C_7$alkenyl or halogen-substituted $C_3$-$C_7$alkenyl; unsubstituted or substituted $C_3$-$C_7$alkynyl; and n is 0, 1, 2, 3 or 4.

* * * * *